(12) United States Patent
Ichihara et al.

(10) Patent No.: US 10,092,187 B2
(45) Date of Patent: Oct. 9, 2018

(54) PHOTOACOUSTIC WAVE MEASURING APPARATUS

(75) Inventors: Shigeru Ichihara, Tokyo (JP); Shuichi Kobayashi, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 670 days.

(21) Appl. No.: 13/820,680

(22) PCT Filed: Sep. 6, 2011

(86) PCT No.: PCT/JP2011/004972
§ 371 (c)(1),
(2), (4) Date: Mar. 4, 2013

(87) PCT Pub. No.: WO2012/042753
PCT Pub. Date: Apr. 5, 2012

(65) Prior Publication Data
US 2013/0160559 A1    Jun. 27, 2013

(30) Foreign Application Priority Data

Sep. 28, 2010    (JP) ................................ 2010-216624

(51) Int. Cl.
*G01N 21/17* (2006.01)
*A61B 5/00* (2006.01)
*G01N 29/24* (2006.01)

(52) U.S. Cl.
CPC .......... *A61B 5/0064* (2013.01); *A61B 5/0091* (2013.01); *A61B 5/0095* (2013.01);
(Continued)

(58) Field of Classification Search
CPC .................................................... A61B 5/00
(Continued)

(56) References Cited

U.S. PATENT DOCUMENTS

| 7,559,897 | B2 * | 7/2009 | Cerofolini | ..................... 600/459 |
| 8,342,028 | B2 | 1/2013 | Ichihara et al. | ................ 73/643 |

(Continued)

FOREIGN PATENT DOCUMENTS

| EP | 1671589 A1 * | 9/2004 | ............... A61B 8/08 |
| EP | 2002784 A1 * | 5/2008 | ............... A61B 5/00 |

(Continued)

OTHER PUBLICATIONS

Frenz et al. Optimization of tissue irradiation in optoacoustic imaging using a linear transducer: theory and experiments. 2008 Proc. SPIE 6856:68561Y-1-68561Y-13.*

(Continued)

*Primary Examiner* — Tse Chen
*Assistant Examiner* — Patrick M Mehl
(74) *Attorney, Agent, or Firm* — Fitzpatrick, Cella, Harper & Scinto (57) ABSTRACT

A photoacoustic wave measuring apparatus, having: a probe including a plurality of devices which detect an acoustic wave generated by irradiating light onto an object; and a signal processor which acquires information about the object on the basis of an acoustic wave received by the devices, wherein the light is irradiated onto the object from the probe side; the probe includes: bright-field devices having a view angle covering a bright-field illumination area, which is an area where the light is irradiated, on the probe-side surface of the object; and dark-field devices having a field of view which does not cover the bright-field illumination area; and the signal processor uses an acoustic wave received by the dark-field devices when acquiring information about the object on the basis of a acoustic wave received before a predetermined time period is elapsed since the irradiation of light onto the object.

24 Claims, 7 Drawing Sheets

(52) U.S. Cl.
CPC ....... *A61B 5/4312* (2013.01); *G01N 21/1702* (2013.01); *G01N 29/2418* (2013.01)

(58) Field of Classification Search
USPC .......................................................... 73/655
See application file for complete search history.

(56) References Cited

U.S. PATENT DOCUMENTS

| | | | |
|---|---|---|---|
| 8,397,573 B2 | 3/2013 | Kobayashi | 73/596 |
| 2002/0097406 A1* | 7/2002 | Fielden | G01N 21/211 356/630 |
| 2006/0184042 A1 | 8/2006 | Wang et al. | 600/476 |
| 2007/0016020 A1 | 1/2007 | Oshiki et al. | 600/437 |
| 2010/0053618 A1 | 3/2010 | Nakajima et al. | 356/432 |
| 2012/0318066 A1 | 12/2012 | Ichihara et al. | 73/655 |

FOREIGN PATENT DOCUMENTS

| | | | | |
|---|---|---|---|---|
| JP | 2001-276064 A | 10/2001 | | |
| JP | 2010-075681 A | 4/2010 | | |
| WO | WO 2005/032374 A1 | 4/2005 | | |
| WO | WO-2008065561 A1 * | 6/2008 | | A61B 8/08 |
| WO | WO 2009/055705 | 4/2009 | | |
| WO | WO 2010/024290 A1 | 3/2010 | | |

OTHER PUBLICATIONS

Hu et al. Neurovascular photoacoustic tomography. 2010 Front. Neuroener. 2:1-7.*
Hu Optical resolution photoacoustic microscopy Jan. 2010 All Theses and Dissertations Paper 162 PhD Thesis Washington University in St Louis—Washington University Open Scholarship, http://openscholarship.wustl.edu/etd 156 pages.*
Manohar et al. The Twente photoacoustic mammoscope: system overview and performance. 2005 Phys.Med.Biol. 50:2543-2557.*
Maslov et al. Photoacoustic imaging of biological tissue with intensity-modulated continuous-wave laser. 2008 J. Biomed. Optics 13: 024006-1-024006-5.*
Wang. Tutorial on Photoacoustic Microscopy and Computer Tomography. 2008 IEEE J. Selected Top. Quant. Electronics 14:171-179.*
Wang. Multiscale photoacoustic microscopy and computed tomography. 2009 Nature Photonics 3:503-509.*
Zhang et al. Functional acoustic microscopy for high resolution and noninvasive in vivo imaging. 2006 Nature Biotech. 24:848-851.*
Yocky. 1995 J. Opt. Soc. Am. A12:1834-1841.*
Hu et al. 2010 Frontiers in Neuroenergetics 2:1-7.*
Bitton 2007 "A high frequency array-based photoacoustic microscopy imaging system" Ph.D Thesis Dissertation University of Southern California—Biomedical Engineering 137 pages.*
S. Manohar et al., "Region-of-Interest Breast Studies Using the Twente Photoacoustic Mammoscope (PAM)", *Proc. of SPIE*, vol. 6437, pp. 643702-1 through 643702-9 ( ).

* cited by examiner

PHOTOACOUSTIC WAVE MEASURING APPARATUS

TECHNICAL FIELD

The present invention relates to a photoacoustic wave measuring apparatus which acquires information about, and creates an image of a living organism.

BACKGROUND ART

Recently, photo-acoustic tomography has been proposed which determines the distribution of an optical characteristics value in a living organism, with good accuracy, by using the characteristics of an acoustic wave (typically, an ultrasound wave) that produces little scattering inside a living organism compared to light (see Non Patent Literature 1). In the present specification, photo-acoustic tomography is referred to as "PAT".

When pulse light generated by a light source is irradiated onto a living organism, the pulse light propagates while diffusing in the living organism. An absorbing body contained in the living tissue absorbs energy of the propagated pulse light and generates an acoustic wave. By analyzing this acoustic wave signal, it is possible to obtain an optical characteristics distribution inside the living organism, and in particular, a distribution of the light absorption density.

One reported clinical application of PAT is photo-acoustic mammography (referred to as "PAM" in the present specification). A PAM apparatus detects a position of a tumor in a breast, principally by creating an image of new blood vessels created in the area of a tumor when a tumor is formed, and a region of high absorption coefficient including the new blood vessels. In one example of a reported PAM apparatus, a breast is sandwiched between two parallel flat plates which are located substantially in parallel, an ultrasound wave probe is disposed on one flat plate, and a light beam is irradiated from the other, opposing flat plate (in the present specification, this is known as "front detection type PAT") (see Non Patent Literature 1).

Moreover, a photoacoustic wave microscope for observing living organisms which uses photoacoustic wave technology has been reported (see Patent Literature 1). In a photoacoustic wave microscope, an ultrasound wave probe which forms a detector and pulse light which is irradiated onto the living organism are disposed on the same side of the living organism (in the present specification, this is referred to as "rear detection type PAT"). The interface region between the ultrasound wave probe and the living organism is not illuminated directly, and the vicinity of the surface of the living organism is depicted in high definition.

In the prior art example of a rear detection type PAT described in Patent Literature 1 mentioned above, it is possible to observe a local position in the vicinity of the surface of the living organism, with high definition. However, since the interface region between the ultrasound wave probe and the living organism is not illuminated directly, then the use efficiency of the light in the deep portions of the living organism is diminished. Therefore, the method described in Patent Literature 1 has a problem in that it is not suitable for objects which require observation in a broad range, up to an including deep portions of the object, such as a breast. In response to this, in recent years, there has been investigation into a method which appends a rear detection mechanism to a PAM apparatus having the composition of the front detection type PAT described in Non Patent Literature 1, and irradiates light from both surfaces of a breast.

CITATION LIST

Patent Literature

[PTL 1]
U.S. Patent Application Publication No. 2006/0184042

Non Patent Literature

[NPL 1]
S. Manohar et al, Proc. of SPIE vol. 6437 643702-1

SUMMARY OF INVENTION

Technical Problem

However, in a bright-field illumination method which illuminates a position opposing an ultrasound wave probe with a rear detection type of composition, there is a problem of reduced detection sensitivity due to the fact that the large photoacoustic wave signal generated from the interface of the irradiated region affects the signal from shallow portions of inside the living organism.

The present invention was devised in view of the problems described above, an object thereof being to provide technology for performing suitable image construction at various depths in an object, while reducing the effects of an interface signal, when performing photoacoustic wave measurement.

Solution to Problem

This invention provides a photoacoustic wave measuring apparatus, comprising:
a probe including a plurality of devices which receive an acoustic wave generated by irradiating light onto an object; and
a signal processor which acquires information about the object on the basis of an acoustic wave received by the devices, wherein
the light is irradiated onto the object from the probe side;
the probe includes:
bright-field devices having a view angle covering a bright-field illumination area, which is an area where the light is irradiated, on the probe-side surface of the object; and
dark-field devices having a field of view which does not cover the bright-field illumination area; and
the signal processor uses an acoustic wave received by the dark-field devices when acquiring information about the object on the basis of a acoustic wave received before a predetermined time period is elapsed since the irradiation of light onto the object.

This application also provides a photoacoustic wave measuring apparatus, comprising:
a probe including a plurality of devices which receive an acoustic wave generated by irradiating light onto an object; and
a signal processor which acquires information about the object on the basis of an acoustic wave received by the devices, wherein
the light is irradiated onto the object from the probe side;
the probe includes:
bright-field devices having a view angle covering a bright-field illumination area, which is an area where the light is irradiated, on the probe-side surface of the object; and dark-field devices having a field of view which does not cover the bright-field illumination area; and the signal processor acquires information about the object by using an acoustic wave received by the bright-field devices and an acoustic wave received by the dark-field devices, respectively at predetermined contribution rates, the contribution rate of the acoustic wave received by the bright-field devices becoming larger than that of the acoustic wave received by the dark-field devices as time elapses after the irradiation of light onto the object.

Advantageous Effects of Invention

According to the present invention, it is possible to provide technology for performing suitable image construction at various depths inside an object while reducing the effects of an interface signal, when performing photoacoustic wave measurement.

Further features of the present invention will become apparent from the following description of exemplary embodiments with reference to the attached drawings.

DESCRIPTION OF EMBODIMENTS

A concrete embodiment of the present invention is described below. In the present embodiment, a photo-acoustic mammography (PAM) apparatus which secures and diagnoses a breast is given as an example of a photoacoustic wave measuring apparatus. Object information refers to information reflecting variation in the acoustic impedance of the internal tissue of the object, the distribution of acoustic wave generating sources, the distribution of the initial sound pressure inside the object, or the distribution of the light energy absorption density which is derived from the initial sound pressure distribution, the absorption coefficient distribution, and the density distribution of the material which constitutes the tissue. The material density distribution is, for example, the oxygen saturation distribution, the oxidized or reduced hemoglobin density distribution, and the like. In the photoacoustic wave measuring apparatus, the object information data may be numerical data of various types described above, for example, or it may be data for forming an image of an object by visualizing the numeral data of various types.

The PAM is constituted by an illumination optical system including a light source, which illuminates an object, an ultrasound wave probe which includes a plurality of ultrasound wave devices, and a parallel plate which secures and holds an object. The method of securing and holding a breast may employ a method where the breast is secured and held using parallel flat plates from the side faces of the breast, or a method where the breast is secured and held using a flat plate from the front face of chest region so as to press against the whole of the breast, or the like.

The basic composition of the photoacoustic wave measuring apparatus is now described with reference to FIG. 1 and FIG. 2.

Figure 1:
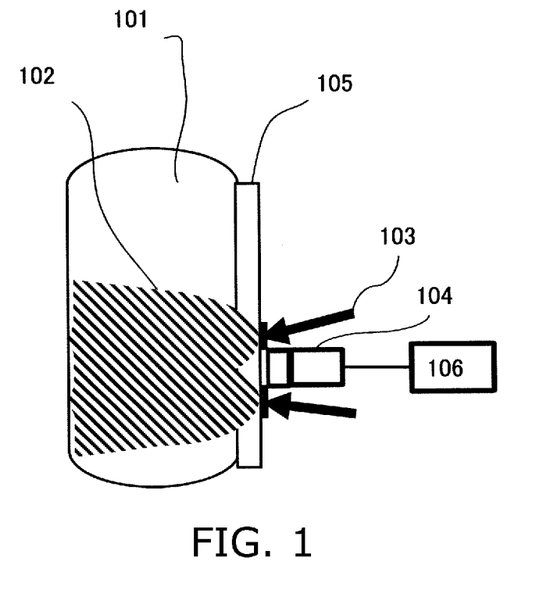
FIG. 1 is a schematic diagram of a PAM apparatus using a rear detection arrangement.

The photoacoustic wave measuring apparatus in FIG. 1 employs a rear detection type of arrangement in which an ultrasound wave probe 104 and an illumination system 103 are arranged on the opposite side of a flat plate 105 from a breast 101 which forms an object. Illumination light is irradiated into the object from the side of the ultrasound wave probe 104, as indicated by 102. The apparatus has a signal processor 106 which amplifies and digitally converts the signal received by the ultrasound wave probe and performs image construction, and the like.

Figure 2:
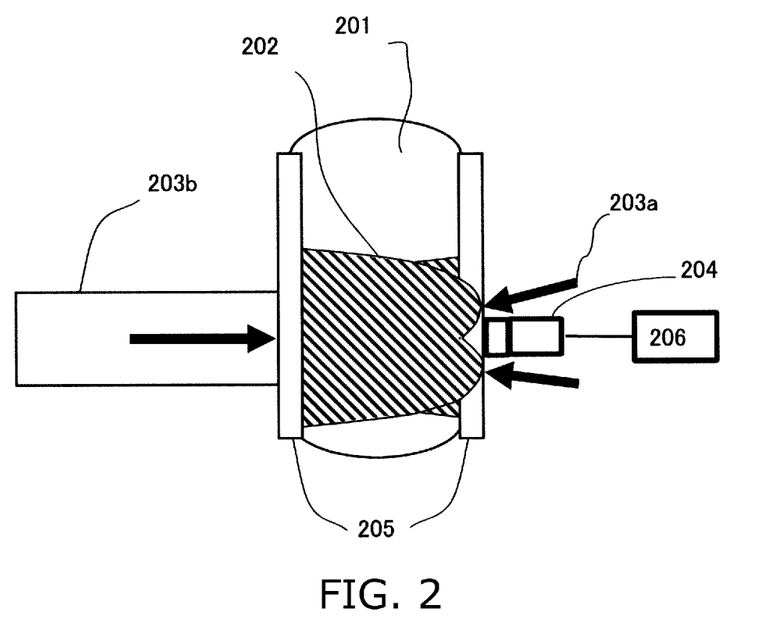
FIG. 2 is a schematic diagram of a PAM apparatus using a double-side irradiation arrangement.

The photoacoustic wave measuring apparatus in FIG. 2 adopts a double-side irradiation arrangement in which a breast 201 is sandwiched between two parallel flat plates 205 and an illumination system 203a, 203b is disposed on either surface thereof. This means that an illumination system is also provided on the flat plate on the opposite side to the ultrasound wave probe. The ultrasound wave probe 204 is arranged on one of the flat plates 205. Irradiation light is shined into the interior of the object as indicated by 202. The apparatus has a signal processor 206 which amplifies and digitally converts the signal received by the ultrasound wave probe and performs image reconstruction, and the like.

The present invention can also be applied to an apparatus using any arrangement. The flat plate and the detection side surface of the ultrasound wave probe are arranged substantially in parallel with each other. Here, substantially parallel means parallel to an allowable degree, on the basis of the surface accuracy and parallelism of the flat plates and the sensor surface, and the mechanical accuracy during assembly of the apparatus.

The ultrasound wave probe is constituted by a plurality of ultrasound wave devices, and can employ an ultrasound wave probe based on a piezoelectric effect, light resonance or capacitance change. In particular, it is common to use an ultrasound wave probe based on a piezoelectric effect using PZT (lead zirconate titanate), and the probe sends and receives acoustic waves by using a piezoelectric diagram having electrodes attached to the front and rear surfaces. When a voltage is applied to the piezoelectric diaphragm, the diaphragm vibrates and radiates an acoustic wave. On the other hand, when the piezoelectric diaphragm is placed in a sound field, a voltage proportional to the sound pressure is generated.

Figure 3:
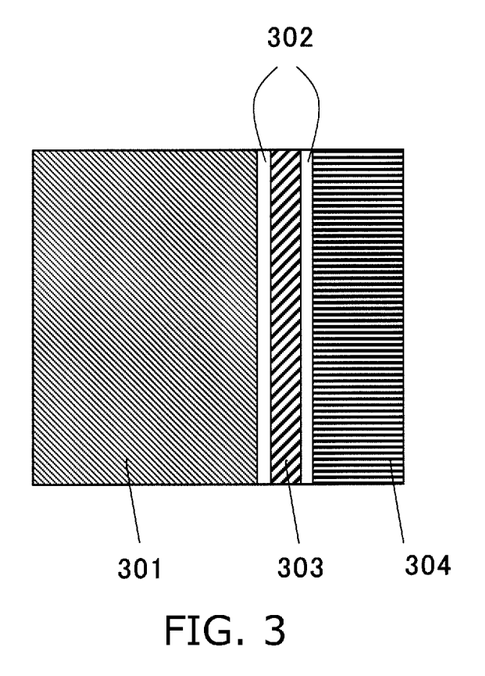
FIG. 3 is a schematic drawing of an ultrasound wave probe including a piezoelectric element.

FIG. 3 is a schematic drawing of an ultrasound wave probe including a piezoelectric element. As shown in FIG. 3, a diaphragm 303 (piezoelectric element) is sandwiched between electrodes 302, and a matching layer 304 is inserted on the front surface in order to transmit the sound pressure caused by the vibration of the diaphragm efficiently to the object. A packing material 301 for suppressing resonance in the diaphragm 303 is attached to the rear surface. If there is no packing material 301, due to resonance of the diaphragm 303, the transmitted and received waveforms contain a large amount of ringing, and the resolution of distance and direction become worse. In particular, in an ultrasound wave probe which uses a piezoelectric element, the acoustic impedance (z) of the members inside the ultrasound wave probe varies and therefore it is difficult to eliminate ringing based on the received signal, if a strong pulse signal is received. Furthermore, the resolution of distance declines, the lower the central frequency of the ultrasound wave probe.

A photoacoustic wave measuring apparatus can determine various information about the interior of the object by performing signal processing of the ultrasound wave measured by the ultrasound wave probe as described above. For example, the intensity of the signal generated at a point of interest in the object is determined by carrying out calculation processing in accordance with the distance to the point of interest in the object, on the basis of the intensity of the ultrasound waves received respectively by the ultrasound wave devices included in the ultrasound wave probe.

Here, the initial signal $P_i$ of the photoacoustic wave is expressed by Formula (1) below.
[Math. 1]

$$P_1 = \Gamma \cdot \mu a \cdot \Phi \quad (1)$$

where, $\Gamma$ is the Gruneisen coefficient.

$\mu a$ is the absorption coefficient of the absorbing body.

$\Phi$ is the amount of light in a local region.

The Gruneisen coefficient is an elastic characteristics value, and is derived by taking the product of the volume elastic coefficient and square of the speed of sound (c), and dividing by the specific heat (Cp). The amount of light means the amount of light irradiated onto the absorbing body.

Consequently, it is possible to calculate the absorption coefficient at the point of interest, by determining the initial signal from the point of interest inside the object, by signal processing, and by determining the amount of light taking account of attenuation by the object. By carrying out this process in respective locations inside the object, it is possible to construct an image of the object in accordance with the absorption coefficient distribution. The absorption coefficient distribution reflects the physical distribution of oxidized hemoglobin, or the like, in the case of a living organism, for example, and therefore enables the internal state of the object to be identified by image construction.

Since the light source irradiated onto the object is diffused inside the living organism, then the amount of light in Formula (1) decreases progressively toward the deeper portions from the surface of the object. In other words, in a rear determination type of apparatus, the amount of illumination light is a maximum value in the illuminated region of the object interface portion. On the other hand, the intensity of the generated photoacoustic wave decreases as the wave propagates inside the living organism. In other words, on the probe side in a rear determination type of apparatus or a double-side irradiation type of apparatus, the photoacoustic wave signal generated by the object interface is close to the ultrasound wave probe, and hence there is little attenuation of the signal. Therefore, the photoacoustic wave signal from the object interface is an extremely strong signal.

In the present embodiment, the object interface is the interface between the flat plate which is substantially parallel to the ultrasound wave probe and the object. Consequently, the photoacoustic wave signal generated by the object interface has a matching phase and behaves like a planar wave, forming an extremely strong pulse signal. As a result of this, strong ringing occurs inside the ultrasound wave probe due to the photoacoustic signal generated at the object interface, and it is difficult to distinguish a photoacoustic wave signal generated from a shallow portion of the living organism (a portion close to the probe).

Next, bright-field illumination and dark-field illumination will be described. The object illumination method is divided into bright-field illumination which irradiates light directly onto a measurement area, and dark-field illumination which does not irradiates light directly onto the measurement area. Dark-field illumination is a technique which is used generally in microscopes. The beam of light which illuminates the sample is irradiated obliquely rather than along the center of the optical axis, in such a manner that the beam of light does not enter directly into the field of view, but rather only light reflected or diffracted at the sample enters into the optical axis.

Figure 4A:
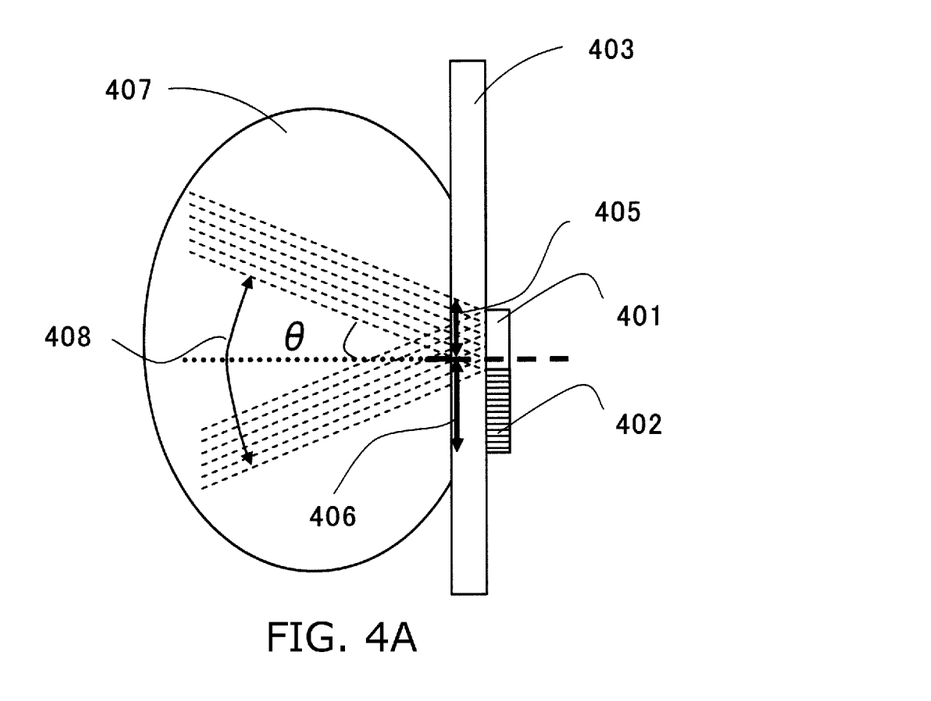
FIGS. 4A and 4B are illustrative diagrams of a bright-field region and a dark-field region.
Figure 4B:
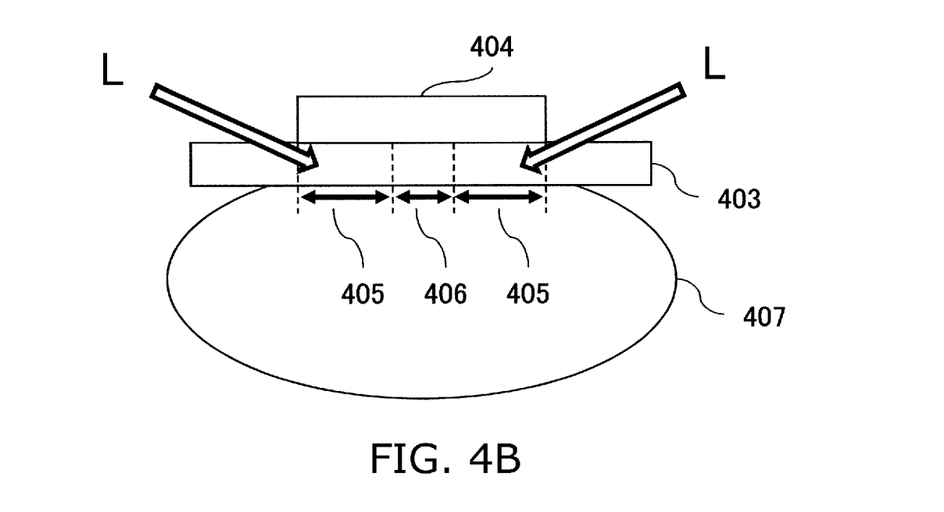

FIG. 4B is a diagram showing circumstances where a bright-field illumination area and a dark-field illumination area are formed in the object, during measurement by a rear detection type of apparatus. A flat plate 403 having a uniform thickness is situated between the object 407 and the ultrasound wave probe 404. Therefore, the light (L) irradiated from the rear side of the ultrasound wave probe 404 is transmitted through the flat plate and is also irradiated onto the object interface which opposes the ultrasound wave probe. The surface region of the object 407 which the illumination light reaches forms a bright-field illumination area 405, and the region which the illumination light does not reach forms a dark-field illumination area 406.

Alternatively, in order to provide a bright-field illumination area, light can be guided to a region opposing the ultrasound wave probe, using an optical fiber, or the like, and irradiated onto the object.

The illumination method according to the present invention is described now with reference to FIG. 4A. In FIG. 4A, a region where light is irradiated directly onto the interface between the object 407 and the flat plate 403 forms a bright-field illumination area 405, and a region where light is not irradiated directly forms a dark-field illumination area 406. An ultrasound wave device disposed in a position opposing the bright-field illumination area 405 is called a bright-field device 401, and an ultrasound wave device disposed in a position opposing the dark-field illumination area 406 is called a dark-field device 402.

Looking at this configuration in detail, the boundary position between the bright-field devices 401 and the dark-field devices 402 and the boundary position between the bright-field illumination area 405 and the dark-field illumination area 406 do not necessarily coincide with each other. Here, the arrangement of devices is set by taking account of the view angle of the bright-field device which is positioned at the boundary with the dark-field devices. In other words, as indicated by reference numeral 408 in FIG. 4, the end position of the field of view on the object interface of the bright-field device which is disposed at the boundary with the dark-field devices forms the boundary between the bright-field illumination area 405 and the dark-field illumination area 406. By adopting this configuration, the entire area in front of the bright-field devices 401 is a bright-field illumination area 405. On the other hand, at least a portion of the dark-field illumination area 406, in addition to the bright-field illumination area 405, comes within the view angle of the bright-field devices 401.

The ultrasound wave devices have directional properties, the sound pressure propagated perpendicularly (at 0 degrees) being the maximum sound pressure in each device and the intensity declining progressively as the angle of propagation increases. The directionality depends on the size and shape of the device, the presence or absence of an acoustic lens, and the like. In the present embodiment, the angle within which a signal can be received at an intensity of up to ½ of the maximum sound pressure is taken to be the view angle. This view angle is used as a basis for determining the boundary between the bright-field devices 401 and the dark-field devices 402 which was described above.

The positions of the bright-field devices 401 and the dark-field devices 402 change with the directionality of the devices used, and the thickness of the flat plate between the ultrasound wave probe and the living organism.

Figure 5:
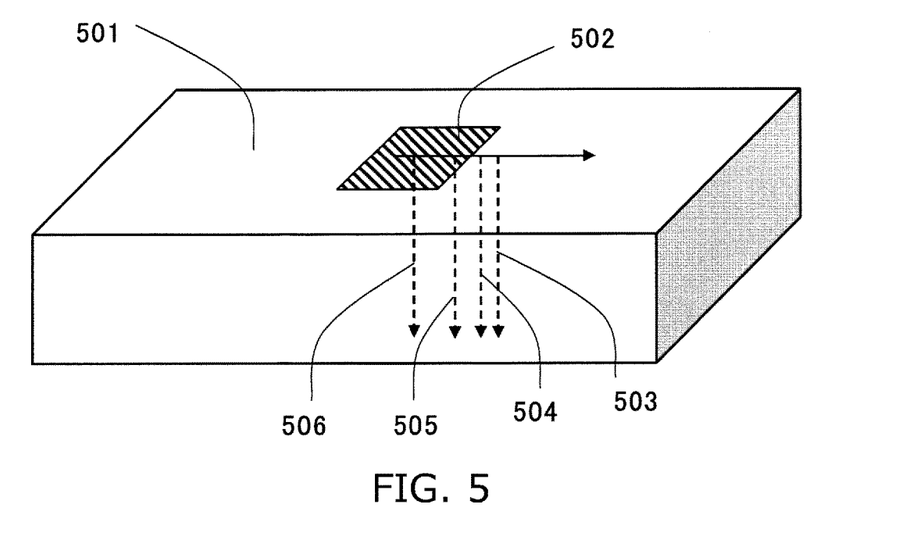
FIG. 5 is a schematic drawing using a simulation of the light amount distribution.

FIG. 5 is a schematic drawing using a simulation of the light amount distribution. A model object 501 which forms the object in the simulation has optical characteristics which are similar to the known values of the optical constants of a living organism. The light beam 502 irradiated onto the model living organism has a uniform light amount distribution in a 50 mm square. Here, the light distribution in a case where the light beam 502 is irradiated onto the model living organism 501 was verified by a Monte Carlo simulation.

The amount of light at the position 504 which is 5 mm to the outside of the boundary of the illumination area boundary on the object surface is no more than ⅕ of the amount of light at the position 505 which is 5 mm to the inside of the boundary of the illumination area boundary, and the amount of light at position 503 which is 10 mm to the outside of the boundary is no more than 1/10 of the amount of light at position 505. This indicates that light also reaches outside the illumination area, due to the effects of rearward scattering in the living organism, but the intensity of this light is greatly attenuated compared to the region inside the illumination area.

On the other hand, the amount of light is substantially the same at the position 504 which is 5 mm outside the boundary of the illumination area of the object surface and at a point 15 mm perpendicularly inside the deep portion of the object from the position 506 which is 25 mm inside the boundary of the illumination area (a position at the center of the illumination area). This indicates that although the amount of light is reduced by scattering in the deep portion of the object, a relatively large amount of light can be obtained in a position in front of the illumination area on the object interface (the deep portion of the object).

As the simulation results described above show, in the bright-field illumination area on the object interface, the amount of light is extremely high and the photoacoustic signal generated from this area is very strong. Therefore, at the ultrasound wave devices in the bright-field area, ringing occurs due to the interface signal. As a result of this ringing, the measurement sensitivity is reduced in the shallow portion of the object which is positioned near to the bright-field illumination area on the object interface. On the other hand, ringing is attenuated periodically in accordance with the structure of the probe, and therefore the effects of ringing in the deep portion are very slight. In other words, when the attenuated intensity is smaller than the background signal intensity of the object, the effects on the SN ratio of the acquired signal are very slight.

Moreover, the deep portion of the object in front of the bright-field illumination area on the object interface has a greater illumination intensity than the deep portion of the object in front of the dark-field illumination area, and therefore it is possible to obtain a photoacoustic signal of high signal intensity. Therefore, it is possible to detect, efficiently, the signal from the deep portion of the object which suffers little effects of the ringing signal, by means of the bright-field devices.

As revealed by the results of the simulation described above, even in the dark-field illumination area on the object interface, at positions near to the bright-field area, an illumination intensity is obtained due to rearward scattering of the light irradiated inside the living organism. However, the illumination intensity decreases the further the position from the bright-field area on the object interface. The light irradiated onto the object is gradually diffused in the depth direction, but the area in front of the dark-field illumination area on the object interface has a low irradiation intensity compared to the bright-field illumination area. Accordingly, in the dark-field devices, there is no photoacoustic wave signal generated from the light irradiated directly onto the object interface, and hence there is little noise, such as ringing, caused by the interface, and the signal from the shallow portion of the living organism can be determined efficiently.

By constructing an image efficiently using the light intensity characteristics in the dark-field illumination area and the bright-field illumination area described above, it is possible to acquire information about a living organism based on a photoacoustic signal which contains little noise. Here, in the ultrasound wave devices of the ultrasound wave probe, the dark-field devices shown in FIG. 4A described above are called "device group A" and the bright-field devices 401 are called "device group B".

Figure 6:
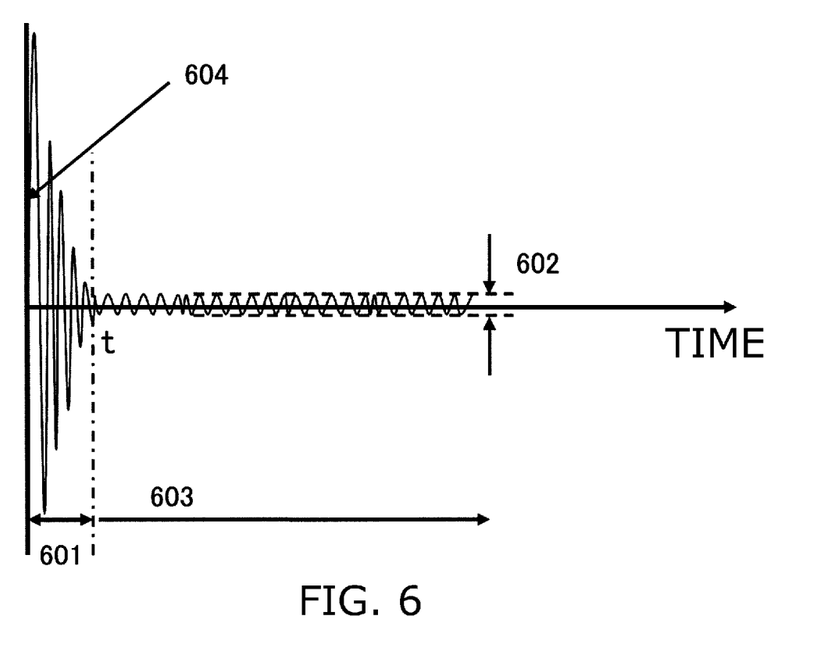
FIG. 6 is an illustrative diagram of a photoacoustic wave signal in a bright-field device.

FIG. 6 shows a photoacoustic wave signal detected by device group B, which are bright-field devices. When processing the detection signal from device group B, either the signal intensity is taken to be 0, or the signal is not used, until a time t when the signal 601 based on ringing which is generated by the interface signal 604 has assumed the same intensity as the background signal 602 of the object. The background signal is a signal which is produced by activity of the object, or the like, and is detected, when there are no effects of light irradiation. The time period until a time t has passed from irradiation of light corresponds to the predetermined time period of the present invention.

It is possible to depict a satisfactory photoacoustic signal distribution by constructing an image using the signal 603 from device group B after time t, and the signal obtained from the device group A which are dark-field devices. Here, the signal acquired by device group A suffers little effects due to ringing, and can therefore be used in image construction, even in the time period corresponding to signal 601 in FIG. 6. If the living organism has a broad area, then a signal is acquired by scanning the ultrasound wave probe. It is possible to measure the whole of the living organism by measuring the photoacoustic signal while scanning a desired region, without changing the illumination area with respect to the ultrasound wave probe.

Furthermore, it is also possible to adopt a method in which the contribution rate of the type of device used in image construction is gradually changed in accordance with the time, rather than instantaneously switching the type of device used for image construction at time t. For example, there is a method in which an image is constructed by using a signal received by the dark-field devices in the shallow region of the object (a region near to the probe), using a signal received by the bright-field devices in the deep region of the object, and using signals from both devices at a ratio corresponding to the depth, in the intermediate region of the object.

In the ultrasound wave devices of the ultrasound wave probe, elements having different characteristics may be used for the bright-field devices and the dark-field devices. Below, the desirable characteristics of the respective devices are described.

Desirably, the devices situated in the bright-field area are able to detect signals from deeper parts of the object. Therefore, it is desirable to use a probe having small transmission loss in the sound pressure and a low central frequency. Furthermore, although there are no particular restrictions on the device shape or the probe shape, if the ultrasound wave probe is small, then there are limits on the living organism information which can be measured at one time, and the measurement time becomes long when measuring a large range. Therefore, when acquiring information about a living organism over a relatively broad range, as with a breast, it is desirable to have a two-dimensional probe having a large device shape.

The device size and the resolution are directly proportional; for instance, a resolution of approximately 2 mm is obtained if measurement is carried out with devices in a 2 mm square pitch. Therefore, supposing that the measurement object is a malignant tumor in a breast and the detection of new blood cells relating to a tumor, then the upper limit of the device size is no more than 5 mm square, desirably, 2 mm square, and more desirably, about 1 mm square. The suitable device size referred to here indicates a case where the purpose of measurement is aimed about achieving a broad measurement object and shortening the measurement time. For example, a two-dimensional configuration of devices is used, consisting of square-shaped ultrasound wave devices which are 1 mm square, envisaging a central frequency of 1 MHz and a resolution of about 1 mm. If the purpose is to measure a limited area with high definition, then a smaller device size is desirable.

For the devices disposed in the dark-field area, it is desirable to use devices having a high central frequency which are capable of measurement at high resolution. Furthermore, although there are no particular restrictions on the device shape, since the dark-field devices detect a signal from a portion with a low amount of light, then if the device shape is large, the signal intensity decreases due to the separation from the illumination area. Therefore, it is desirable to use a relatively small probe, such as a linear array, as employed in ultrasound diagnosis.

In particular, if a 126-row linear array, or the like, having a central frequency of 7 MHz or higher is used, then it is possible to acquire an echo image by sending and receiving ultrasound waves to and from a living organism. In this case, the present apparatus can be formed as a multi-modality apparatus which measures an acoustic wave image and an ultrasound wave image.

Figure 7A:
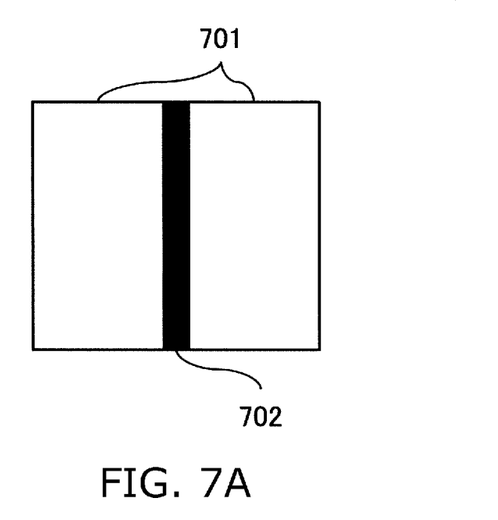
FIGS. 7A and 7B are diagrams showing an example of the arrangement of devices in an ultrasound wave probe.

FIG. 7A is a diagram showing the probe described above as viewed from the side including the ultrasound devices, in other words, the side adjacent to the flat plate. The devices 702 arranged in the dark-field area have a linear shape following the central line of the probe. Bright-field devices 701 are positioned on either side of these dark-field devices.

Furthermore, a composition must also be adopted in which the dark-field devices do not acquire the very large signal from the interface region. Therefore, if the directionality of the dark-field devices is broad in relation to the bright-field devices, it is also desirable to limit the view angle by providing an acoustic lens, or the like, on the front faces of the devices.

Figure 7B:
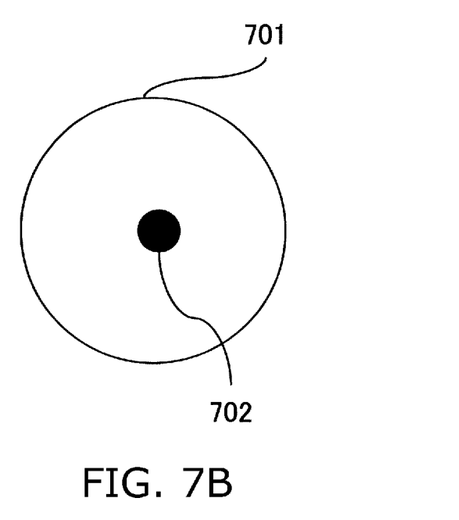

The overall arrangement of the devices, in other words, the dark-field arrangement and the bright-field arrangement, can be chosen freely in accordance with the bright-field area where the object is illuminated. It is also possible to use an ultrasound wave probe in which devices are arranged in a circular shape, rather than an ultrasound wave probe formed by a collection of square devices. FIG. 7B is an example of a probe in which devices are arranged in a circular shape, the bright-field devices 702 being arranged in the central portion and the dark-field devices 701 being arranged in the peripheral portion.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-216624, filed on Sep. 28, 2010, which is hereby incorporated by reference herein in its entirety.

The invention claimed is:

1. A photoacoustic apparatus, comprising: a probe configured to receive an acoustic wave which is generated by light irradiating an object; and a signal processor configured to acquire information about the object on the basis of the acoustic wave which is received by the probe, wherein the probe includes a bright-field device having a view angle covering a bright-field illumination area, which is an area where the object is irradiated with the light, and a dark-field device having a view angle which does not cover the bright-field illumination area, which are configured to receive the acoustic wave, wherein a first contribution rate for a signal acquired, before a predetermined time period has elapsed since the light irradiation of the object, by said dark-field device is larger than a second contribution rate for a signal acquired, before the predetermined time period has elapsed since the light irradiation of the object, by said bright-field device.

2. The photoacoustic apparatus according to claim 1, wherein a third contribution rate for a signal acquired, after the predetermined time period has elapsed since the light irradiation of the object by said bright-field device is larger than a fourth contribution rate for a signal acquired, after the predetermined time period has elapsed since the light irradiation of the object, by said dark-field device.

3. The photoacoustic apparatus according to claim 1, wherein the predetermined time period is a time period required for attenuating ringing due to an acoustic wave generated in the surface of the object to an intensity of a background signal.

4. The photoacoustic apparatus according to claim 1, wherein said dark-field device has a higher central frequency than said bright-field device.

5. The photoacoustic apparatus according to claim 1, wherein said dark-field device has a smaller size than said bright-field device.

6. The photoacoustic apparatus according to claim 1, wherein said bright-field device is arranged on both sides of said dark-field device.

7. The photoacoustic apparatus according to claim 1, wherein said bright-field device is arranged around the periphery of said dark-field device.

8. The photoacoustic apparatus according to claim 1, further comprising two parallel flat plates configured to sandwich the object.

9. The photoacoustic apparatus according to claim 1, wherein said signal processor is configured to acquire the information about the object for a region within a first depth from the probe, using a signal acquired from said dark-field device and without using a signal acquired from said bright-field device, said signal processor is configured to acquire the information about the object for a region between the first depth and a second depth deeper than the first depth from the probe, using signals acquired from said bright-field device and of said dark-field device, and said signal processor is configured to acquire the information about the object for a region deeper than the second depth, using a signal acquired from said bright-field device and without using a signal acquired from said dark-field device.

10. The photoacoustic apparatus according to claim 1, wherein said signal processor is configured to acquire the information about the object using the signal acquired, before the predetermined time period has elapsed since light irradiation of the object, from said dark-field device and without using the signal acquired, before the predetermined time period has elapsed since light irradiation of the object with light, from said bright-field device.

11. The photoacoustic apparatus according to claim 1, wherein the bright-field device has a view angle covering a bright-field illumination area which is an area where the object is irradiated with the light, the dark-field device has a view angle which does not cover the bright-field illumination area, and the view angle of said dark-field device or said bright-field device is between 0 and a first predetermined angle, wherein the first predetermined angle is an angle that an intensity of a signal received by said dark-field device or said bright-field device when the acoustic wave enters with the first predetermined angle thereto is ½ of an intensity of a signal received by said dark-field device or said bright-field device when the acoustic wave enters perpendicularly.

12. The photoacoustic apparatus according to claim 1, wherein a third contribution rate for a signal acquired, after the predetermined time period has elapsed since the light irradiation of the object, by said dark-field device is smaller than the first contribution rate, and a fourth contribution rate for a signal acquired, after the predetermined time period has elapsed since the light irradiation of the object, by said bright-field device is larger than the second contribution rate.

13. The photoacoustic apparatus according to claim 1, wherein the bright- field device has a view angle covering a bright-field illumination area which is an area where the object is irradiated with the light, and the dark-field device has a view angle which does not cover the bright-field illumination area.

14. A photoacoustic apparatus, comprising: a probe configured to receive an acoustic wave which is generated by light irradiating an object, the object being irradiated with the light from around the probe; and a signal processor configured to acquire information about the object on the basis of the acoustic wave which is generated by light irradiation of the object and is received by the probe, wherein the probe includes a first device and a second device which is arranged more toward a central portion of the probe than the first device, which are configured to receive the acoustic wave, and wherein a first contribution rate for a signal acquired, before a predetermined time period has elapsed since the light irradiation of the object, by said second device is larger than a second contribution rate of a signal acquired, before the predetermined time period has elapsed since the light irradiation of the object, by said first device.

15. The photoacoustic apparatus according to claim 14, wherein said second device has a higher central frequency than said first device.

16. The photoacoustic apparatus according to claim 14, wherein said second device has a smaller size than said first device.

17. The photoacoustic apparatus according to claim 14, wherein said first device is arranged on both sides of said second device.

18. The photoacoustic apparatus according to claim 14, wherein said signal processor is configured to acquire the information about the object using the signal acquired, before the predetermined time period has elapsed since light irradiation of the object, from said second device and without using the signal acquired, before the predetermined time period has elapsed since light irradiation of the object with light, from said first device.

19. The photoacoustic apparatus according to claim 14, wherein a third contribution rate for a signal acquired, after the predetermined time period has elapsed since the light irradiation of the object, by said first device is larger than a fourth contribution rate for a signal acquired, after the predetermined time period has elapsed since the light irradiation of the object, by said second device.

20. The photoacoustic apparatus according to claim 14, wherein said signal processor is configured to acquire the information about the object for a region within a first depth from said probe, using a signal acquired from said second device and without using a signal acquired from said first device, said signal processor is configured to acquire the information about the object for a region between the first depth and a second depth deeper than the first depth from said probe, using signals acquired from said first device and said second device, and said signal processor is configured to acquire the information about the object for a region deeper than the second depth, using a signal acquired from said first device and without using a signal acquired from said second device.

21. The photoacoustic apparatus according to claim 14, wherein a third contribution rate for a signal acquired, after the predetermined time period has elapsed since the light irradiation of the object, by said second device is smaller than the first contribution rate, and a fourth contribution rate for a signal acquired, after the predetermined time period has elapsed since the light irradiation of the object, by said first device is larger than the second contribution rate.

22. A photoacoustic apparatus, comprising: a probe configured to receive an acoustic wave which is generated by light irradiating an object; and a signal processor configured to acquire information about the object on the basis of the acoustic wave which is received by the probe, wherein the probe includes a bright-field device having a view angle covering a bright-field illumination area, which is an area where the object is irradiated with the light, and a dark-field device having a view angle which does not cover the bright-field illumination area, which are configured to receive the acoustic wave, and wherein when said signal processor acquires the information of a region within a first depth from the probe, a first contribution rate for a signal acquired by said dark-field device is larger than a second contribution rate for a signal acquired by said bright-field device.

23. The photoacoustic apparatus according to claim 22, wherein when said signal processor acquires the information of a region deeper than the first depth, a third contribution rate for a signal acquired by said dark-field device is smaller than the first contribution rate and a fourth contribution rate for a signal acquired by said bright-field device is larger than the second contribution rate.

24. The photoacoustic apparatus according to claim 22, wherein the bright-field device has a view angle covering a bright-field illumination area which is an area where the object is irradiated with the light, and the dark-field device has a view angle which does not cover the bright-field illumination area.

* * * * *